United States Patent [19]
Nettleton, Jr. et al.

[11] 4,301,248
[45] Nov. 17, 1981

[54] FERMENTATION PROCESS FOR MAKING RACHELMYCIN

[75] Inventors: Donald E. Nettleton, Jr., Jordon; James A. Bush, Fayetteville; William T. Bradner, Manlius, all of N.Y.

[73] Assignee: Bristol-Myers Company, New York, N.Y.

[21] Appl. No.: 194,202

[22] Filed: Oct. 6, 1980

Related U.S. Application Data

[63] Continuation-in-part of Ser. No. 106,225, Dec. 21, 1979, abandoned, which is a continuation of Ser. No. 15,976, Feb. 28, 1979, abandoned.

[51] Int. Cl.³ ............................................. C12P 17/18
[52] U.S. Cl. .................................... 435/119; 435/128; 435/886
[58] Field of Search ................. 435/119, 128; 424/121

[56] References Cited
U.S. PATENT DOCUMENTS
4,169,888 10/1979 Hanka et al. ........................ 424/121

Primary Examiner—Lionel M. Shapiro
Attorney, Agent, or Firm—David M. Morse

[57] ABSTRACT

A known antibiotic substance designated herein as rachelmycin is produced by fermentation of Streptomyces sp. strain C-329, variant 70 (ATCC 31128) or *Streptomyces anandii* subsp. *arraffinosus* strain C-22, 437 (ATCC 31431). Rachelmycin exhibits both antibiotic and antitumor properties.

4 Claims, 3 Drawing Figures

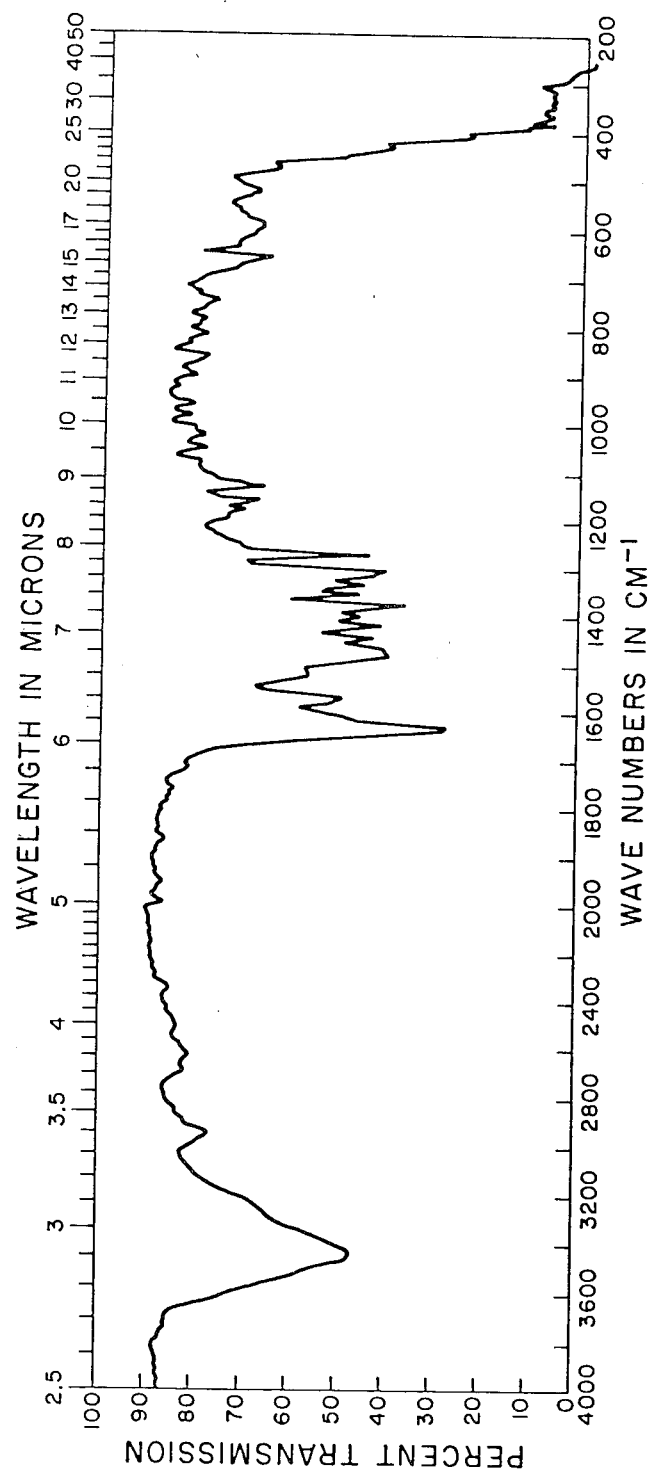
FIG. I
INFRARED SPECTRUM OF RACHELMYCIN (KBr)

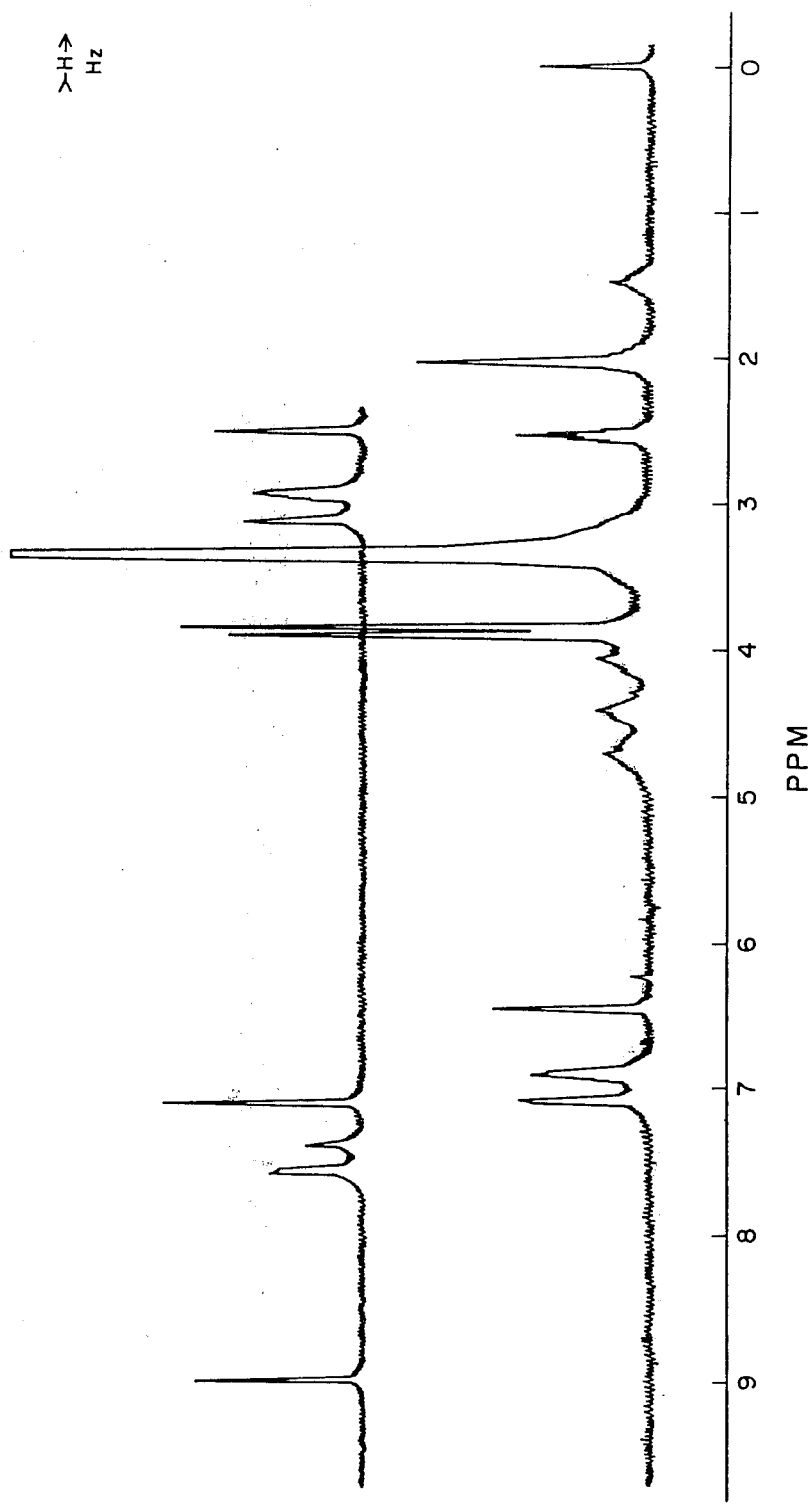

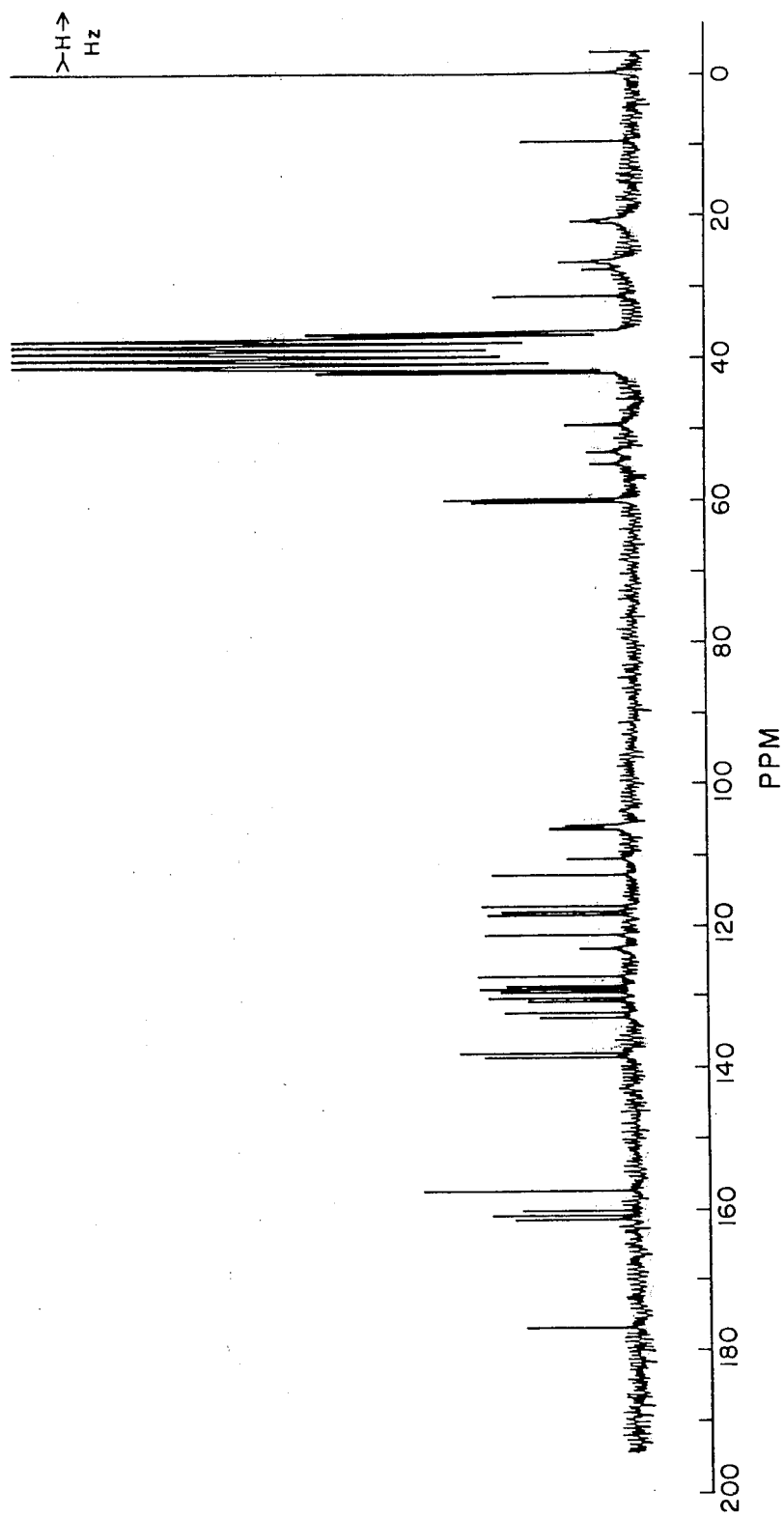

FERMENTATION PROCESS FOR MAKING RACHELMYCIN

CROSS-REFERENCE TO RELATED APPLICATIONS

This application is a continuation-in-part of co-pending application Ser. No. 106,225 filed Dec. 21, 1979, which in turn is a continuation of application Ser. No. 15,976 filed Feb. 28, 1979, both now abandoned.

BACKGROUND OF THE INVENTION

The present invention relates to a new fermentation process for the production of a composition of matter designated rachelmycin. Rachelmycin has been found to be identical with antibiotic CC-1065 disclosed and claimed in U.S. Pat. No. 4,169,888.

SUMMARY OF THE INVENTION

There is provided by the present invention a new process for the preparation of a known antibiotic substance. More particularly, the antibiotic designated rachelmycin by the present inventors is prepared by cultivating certain rachelmycin-producing strains of Streptomyces in an aqueous nutrient medium under submerged aerobic conditions until a substantial amount of rachelmycin is produced and, optionally, isolating the rachelmycin from the culture medium.

DESCRIPTION OF THE DRAWINGS

FIG. 1 shows the infrared absorption spectrum of rachelmycin (in KBr).

FIG. 2 shows the PMR (proton magnetic resonance) spectrum of rachelmycin dissolved in dimethylsulfoxide wherein the chemical shifts are reported in ppm downfield from internal TMS.

FIG. 3 shows the CMR spectrum of rachelmycin dissolved in dimethylsulfoxide wherein the chemical shifts are reported in ppm downfield from internal TMS.

DETAILED DESCRIPTION

The present invention provides a novel fermentation process for a composition of matter designated herein as rachelmycin. Rachelmycin in its essentially pure crystalline form is characterized by the following properties:

(1) It appears in the form of pale yellow needles which have no definite melting point but decompose above 285° C.;

(2) It contains the elements carbon, hydrogen, nitrogen and oxygen and elementary analysis gives the following approximate values: C: 55.86%; H: 5.06%; N: 12.01%; residue: 1.19%;

(3) It has a molecular weight of 703 as determined by field desorption mass spectroscopy;

(4) It is soluble in dimethylsulfoxide, dimethylformamide and tetrahydrofuran, slightly soluble in mixtures of methanol with methylene chloride or chloroform and insoluble in most other common solvents;

(5) When dissolved in methanol at a concentration of 0.010 g/l it shows UV absorption maxima and absorptivities of 233 (sh) (30.5), 257–260 (sh) (26.6 ) and 371 (39.5); in neutral medium 230 (sh) (49.6), 278 (40.9) and 375 (41.8); and in acidic medium 233 (32.8), 257 (27.7), 300 and 360.

(6) When dissolved in DMSO-$d_6$ at a concentration of 1 mg/0.5 ml DMSO-$d_6$, it has a 100 MHz PMR (proton magnetic resonance) spectrum substantially as shown in FIG. 2 with observed chemical shifts and pattern description (measured on Varian Model XL 100 instrument) as follows: 12.96 (s, 1H, exchangeable), 11.54 (bs, 2H, exchangeable), 11.36 (bs, 1H, exchangeable), 11.08 (s, 1H, exchangeable), 7.09 (bs, 2H), 6.91 (bs, 3H), 6.46 (s, 1H), 4.70 (m, 2H), 4.40 (m, 1H), 4.04 ; (m, 2H), 3.89 (s, 3H, OCH$_3$), 3.85 (s, 3H, OCH$_3$), ~3.40 (HOD peak obscuring other signals), 2.02 (bs, 4H) and 1.46 (m, 1H);

(7) When dissolved in DMSO-$d_6$ at a concentration of 20 mg/ml DMSO-$d_6$, it has a 25 MHz CMR ($^{13}$C magnetic resonance) spectrum substantially as shown in FIG. 3 with observed chemical shifts and pattern description (measured on Varian Model XL 100 instrument) as follows: 176.0 (s), 160.8 (s), 160.4 (s), 159.9 (s), (2) 157.2 (s), 138.1 (s), 137.7 (s), 132.7 (s), 132.0 (s), 130.4 (s), 130.1 (s), 129.2 (s), 128.8 (s), 128.7 (s), 127.2 (s), 127.0 (s), 123.3 (d), 121.0 (s), 118.0 (s), 117.5 (s), 117.0 (s), 112.8 (s), 110.3 (d), 106.0 (d), 105.6 (d), 60.1 (q), 59.8 (q), 55.0 (t), 53.1 (t), 49.2 (t), 31.4 (s), 27.5 (t), 26.4 (t), 20.8 (d), 20.6 (d), 9.4 (q);

(8) When pelleted in potassium bromide, it has an infrared absorption spectrum substantially as shown in FIG. 1;

(9) It gives on HPLC analysis using a microporous silica ($\mu$ PORASIL—tradename of Waters Associates Inc., Milford, Mass.)) adsorbent and tetrahydrofuran as the running solvent a k' value of 0.7;

(10) It is effective in inhibiting the growth of various Gram-positive bacteria;

(11) It is effective in inhibiting the growth of Sarcoma 180, P-388 leukemia, L-1210 leukemia, B16 melanoma, Walker 256 carcinosarcoma and Lewis lung carcinoma in rodents; and

(12) It exhibits phage inducing properties.

Rachelmycin produced according to the present invention has been found to be identical with the antibiotic compound CC-1065 disclosed in U.S. Pat. No. 4,169,888 and in *J. Antibiotics* 31 (12); 1211–1217 (1978). Antibiotic CC-1065 has recently been reported as having the structure

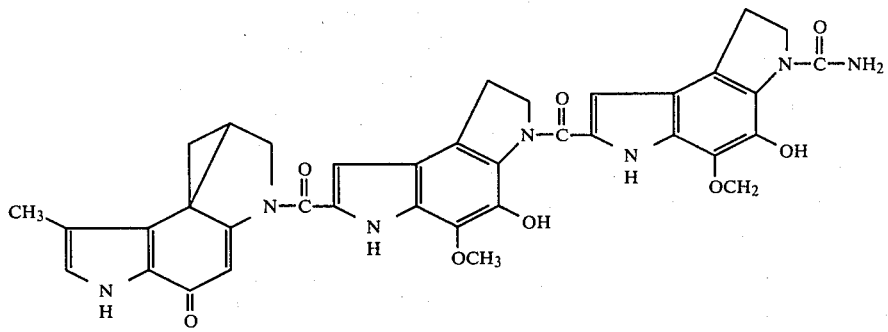

[See page 72 of *Program and Abstracts* of Third International Conference on Organic Synthesis sponsored by the International Union of Pure and Applied Chemistry, University of Wisconsin, June 15–20, 1980 ].

According to the above-mentioned references, antibiotic CC-1065 prepared by fermentation of *Streptomyces zelensis* NRRL 11,183. This organism has been found to differ substantially from the rachelmycin-producing strains of Streptomyces employed in the present invention.

THE PRODUCING ORGANISMS

The rachelmycin antibiotic of the present invention may be prepared by cultivating a rachelmycin-producing strain of Streptomyces sp. having the identifying characteristics of ATCC 31128 or *Streptomyces anandii* subsp. *arraffinosus* having the identifying characteristics of ATCC 31431 in an aqueous nutrient medium under submerged aerobic conditions until a substantial amount of rachelmycin is produced by said organism in said culture medium.

One preferred rachelmycin-producing strain is a variant of a culture isolated from a Manlius, N.Y. manure sample. The parent culture was designated strain C-329 and used to prepare a variant-designated C-329 variant 70 which gave high productivity of rachelmycin. Strain C-329 variant 70 has been deposited in the American Type Culture Collection, Rockville, Md. and added to its permanent collection of microorganisms as ATCC 31128.

Another preferred rachelmycin-producing strain designated strain C-22,437 has been isolated from a Katpadi, Madras, India soil sample. A culture of this organism has been deposited in the American Type Culture Collection under the accession number ATCC 31431.

Characteristics of the above-mentioned preferred producing strains are described in detail below.

STRAIN C-329 VARIANT 70 (ATCC 31128)

Strain C-329 variant 70 forms aerial mycelium and develops straight to flexuous spore-chains with 10–40 spores in a chain. Such spore-chains are predominant on tyrosine agar and yeast extract-malt extract agar. A sclerotic granule, which is oval in shape and 5–15μ in diameter, is formed on inorganic salts-starch agar. The primary mycelium is branched, non-septated and non-fragmented. Spiny spores are observed.

Mass color of the aerial mycellium is light gray. Reverse side of the growth is generally light yellowish brown. A melanoid pigment is produced in tyrosine agar and peptone-yeast extract-iron agar. Any other diffusible pigment than melanoid is not produced. The cultural characteristics are shown in Table 1.

TABLE 1

| Cultural Characteristics of Strain C-329* | | |
|---|---|---|
| | Growth | Reverse Color |
| Sucrose-nitrate agar | Restricted | Light yellowish brown |
| Glucose-asparagine agar | Restricted | Pale brownish yellow |
| Glycerol-asparagine agar | Moderate | Light yellowish brown |
| Inorganic salts-starch agar | Restricted | Dull yellow |
| Tyrosine agar | Good | Brown |
| Nutrient agar | Good | Light brown |
| yeast extract-malt extract agar | Good | Brown |
| Oatmeal agar | Restricted | Colorless |
| Peptone-yeast extract-iron agar | Good | Brown |

| | Aerial Mycelium | Diffusible Pigment |
|---|---|---|
| Sucrose-nitrate agar | Scant, brownish white to light gray | Pale brown |
| Glucose-asparagine agar | Scant, brownish white to light gray | None |
| Glycerol-asparagine agar | Scant, brownish white to light gray | None |
| Inorganic salts-starch agar | Scant, light gray | None |
| Tyrosine agar | Abundant, brownish white to light gray | Light brown |
| Nutrient agar | Abundant, light gray | Light brown |
| Yeast extract-malt extract agar | Abundant, light gray to medium gray | Light brown |
| Oatmeal agar | Poor, light gray | None |
| Peptone-yeast extract iron agar | None or scant, brownish white | Deep brown |

*Observation data after cultivating for 2 weeks at 37° C.

Strain C-329 has considerable tolerance to sodium chloride and grows well in organic media containing up to 4% NaCl. Tyrosinase reaction is positive. D-glucose, L(+)-arabinose, sucrose, D-fructose, D-xylose, inositol and D-mannitol are utilized for growth. Very scant or no growth was obtained with rhamnose, raffinose and cellulose. The physiological characteristics and the carbohydrate utilization are shown in Tables 2 and 3, respectively.

TABLE 2

| Physiological Characteristics of Strain C-329 | | |
|---|---|---|
| Tests | Responses | Methods and materials employed |
| Nitrate reduction in inorganic medium | Weakly positive | Sucrose-nitrate broth |
| Nitrate reduction in organic medium | Strongly positive | The organic medium, recommended by Leudemann |

TABLE 2-continued
Physiological Characteristics of Strain C-329

| Tests | Responses | Methods and materials employed |
|---|---|---|
| Gelatin liquefaction | Positive | Basal medium; Yeast-malt broth which leave agar in ISP No. 2 medium |
| Effect of NaCl in organic medium | Moderate growth at 0.5-4% NaCl and without NaCl. Restricted growth at 8% NaCl. | Basal medium: Yeast-extract-starch agar |
| Growth temperature | Optimal growth at 40-48° C. Moderate growth at 28° C. and 52° C. Restricted growth at 20° C. and 56° C. No growth at 15° C. and 60° C. | ISP No. 2 medium |

TABLE 3
Carbohydrate-utilization of Strain C-329

| | |
|---|---|
| D(−)-Arabinose | − |
| L(+)-Arabinose | + |
| D-Xylose | + |
| D-Ribose | + * |
| L-Rhamnose | − |
| D-Glucose | + |
| D(+)-Galactose | + |
| D-Fructose | + |
| D-Mannose | + |
| Sucrose | + |
| Lactose | + |
| Maltose | + |
| D(+)-Melibiose | − |
| Raffinose | ± |
| D(+)-Melezitose | + * |
| Soluble starch | + |
| Cellulose | − |
| Glycerol | + |
| Inositol | + |
| D-Mannitol | + |
| D-Sorbitol | − |
| Dulcitol | − |

Basal medium: Pridham-Gottlieb medium
* Aerial mycelium is not formed

The morphological, cultural and physiological characteristics of strain C-329 variant 70 indicate that the organism is a species of the genus Streptomyces. Until further characteristics are examined, the strain will be considered an undetermined species of Streptomyces and designated as Streptomyces sp. strain C-329 variant 70.

Strain C-22,437 (ATCC 31431)

Strain C-22,437 forms abundant aerial mycelium and develops aerial spore chains which show generally open spirals with several turns. Also found are short spore chains in hooked or looped shapes as well as spore chains in a closed irregular spiral at the tip. The spore chains are formed on monopodially branched sporophores and contain 10-50 spores in a chain. The spores are oval to cylindrical in shape and have a smooth surface. The aerial mycelium and spore chains are predominantly formed on Czapek's sucrose-nitrate agar, yeast extract-malt extract agar and Bennett's agar.

Some spore chains in coalesced spirals are filled with soft blackish material and develop into black moist globules. The globular spore masses appear to originate at the tip of the sporophore or at the intercalary site of the spore chain and are 5-10μ in diameter. The globules are predominantly formed on yeast extract-malt extract agar. Sclerotic granules which are oval in shape and 5-15μ in diameter are also formed in the substrate mycelium. The substrate mycelium is well-developed, branched and not fragmented.

The cell wall contains LL-diaminopimelic acid and glycine as diagnostic components. The whole cell hydrolyzate contains no diagnostic sugar.

Strain C-22,437 grows moderately on both nutritionally rich organic media and chemically defined media. The mass color of aerial mycelium is brownish gray on Czapek's sucrose-nitrate agar, yeast extract-malt extract agar, oatmeal agar, glycerol-asparagine agar and tyrosine agar, and is light gray on inorganic salts-starch agar. Melanoid pigments are produced on Czapek's sucrose-nitrate agar, tryptone-yeast extract broth, yeast extract-malt extract agar and tyrosine agar. Non-melanoid pigments are not produced. The cultural characteristics of strain C-22,437 are shown in Table 4.

TABLE 4
Cultural Characteristics of Strain C-22,437

| | |
|---|---|
| Czapek's agar (Sucrose-nitrate agar) | G: Abundant<br>R: Dark grayish reddish brown (No. 47)<br>A: Abundant, brownish gray (No. 64) later partially grayish pink (No. 8)<br>D: Dark grayish reddish brown (No. 47) |
| Tryptone-yeast extract broth (ISP No. 1) | G: Moderate, surface-ring growth and sedimented cell mass<br>D: Dark brown (No. 59) |
| Yeast extract-malt extract agar (ISP No. 2) | G: Abundant<br>R: Dark grayish brown (No. 62)<br>A: Abundant, brownish gray (No. 64) and light gray (No. 264)<br>D: Moderate brown (No. 58) |
| Oatmeal agar (ISP No. 3) | G: Poor<br>R: Brownish orange (No. 54)<br>A: Restricted, light brownish gray (No. 63)<br>D: Light yellowish brown (No. 76) |
| Inorganic salts-starch agar (ISP No. 4) | G: Poor<br>R: Light grayish yellowish brown (No. 79)<br>A: Scant, white later light gray (No. 264)<br>D: None |
| Glycerol-asparagine agar (ISP No. 5) | G: Moderate<br>R: Light reddish brown (No. 42)<br>A: Very limited formation, white later light brownish gray (No. 63)<br>D: None |
| Peptone-yeast extract-iron agar (ISP No. 6) | G: Moderate<br>R: Light grayish brown (No. 60)<br>A: None<br>D: Moderate brown (No. 58) |
| Tyrosine agar (ISP No. 7) | G: Abundant<br>R: Grayish brown (No. 61)<br>A: Scant, partial formation, yellowish gray (No. 93) later brownish gray (No. 64)<br>D: Light brownish gray (No. 63) |
| Glucose-ammonium-salts agar | G: Moderate<br>R: Light brownish gray (No. 63)<br>A: Moderate, light gray (No. 264)<br>D: None |
| Bennett's agar | G: Abundant<br>R: Light brown (No. 57) later dark brown (No. 59)<br>A: Abundant, brownish gray (No. 64), partially pale |

TABLE 4-continued

Cultural Characteristics of Strain C-22,437 yellowish pink (No. 31)

Cultivation: 28° C. for 3 weeks
G: Growth, R: Reverse, A: Aerial mycelium, D: Diffusible pigment
Color names were assigned according to "ISCC-NBS Centroid Color Charts", published by U.S. Department of Commerce National Bureau of Standards, Washington, D.C. 20234

Strain C-22,437 grows in the range of 20° to 45° C. but does not grow at 10° and 50°. It does not produce nitrite from nitrate. Gelatin is liquified late. It has considerable tolerance to sodium chloride.

D-Glucose, D-xylose, L-arabinose, D-fructose, D-galactose, D-mannitol, inositol and sucrose are utilized for growth. L-Rhamnose and raffinose are not utilized. The physiological characteristics and carbon utilization are shown in Tables 5 and 6, respectively.

TABLE 5

Physiological characteristics of Strain C-22,437

| | |
|---|---|
| Growth temperature | Growth from 20° to 45° C. No growth at 10° and 50° C. |
| Hydrogen sulfide from L-cysteine | Strongly positive |
| Nitrite from nitrate | Negative (both in organic medium and chemically defined medium) |
| Reactions on milk | No distinct reactions |
| Gelatin liquifaction | Liquefied late |
| Starch hydrolysis | Positive |
| Tolerance to sodium-chloride | Resistant: Growth at 8% NaCl but no growth at 10% NaCl |

(Cultivation: 28° C.)

TABLE 6

Carbon Utilization of Strain C-22,437

| | | | |
|---|---|---|---|
| Glycerol | + | Melibiose | − |
| D-Arabinose | − | Trehalose | + |
| L-Arabinose | + | Raffinose | − |
| D-Xylose | + | D(+)-Melezitose | + |
| D-Rhibose | + | Soluble starch | + |
| L-Rhamnose | − | Dulcitol | − |
| D-Glucose | + | Inositol | + |
| D-Galactose | + | D-Mannitol | + |
| D-Fructose | + | D-Sorbitol | − |
| D-Mannose | + | Salicin | + |
| L(−)-Sorbose | − | Cellulose | − |
| Sucrose | + | Chitin | + |
| Lactose | + | Keratin | + |
| Cellobiose | + | | |

Observation after incubation at 28° C. for 2 weeks
Basal medium: Pridham and Gottlieb's mineral salts The morphological, cultural and physiological characteristics as well as the chemical composition of cells indicate that strain C-22,437 is a species of the genus Streptomyces. When characteristics of strain C-22,437 were compared with those of known species of Streptomyces described in the literature, it appeared most similar to *Streptomyces anandii*. Accordingly, strain C-22,437 has been named *Streptomyces anandii* subsp. *araffinosus* since it differs from *Streptomyces anandii* in not utilizing raffinose.

Since the Streptomyces are easily mutated naturally or artificially, the present invention includes within its scope Streptomyces sp. strain C-329 variant 70, *Streptomyces anandii* subsp. *arraffinosus* strain C-22,437 and all natural and artificial rachelmycin-producing variants and mutants thereof.

PRODUCTION OF RACHELMYCIN

Rachelmycin is produced by cultivating Streptomyces sp. strain C-329 variant 70 (ATCC 31128) or *Streptomyces anandii* subsp. *arraffinosus* strain C-22, 437 (ATCC 31431), or a mutant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts surface cultures and bottles may also be used. The general procedures used for the cultivation of other actinomycetes are applicable to the present invention.

The nutrient medium should contain an appropriate assimilable carbon source such as lactose, glycerol, sucrose, glucose, mannose, fructose, corn starch, etc. As nitrogen sources, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron and the like.

Production of the rachelmycin antibiotic can be effected at any temperature conducive to satisfactory growth of the producing organism, e.g. 20°-45° C., and is conveniently carried out at a temperature of around 27°-32° C. Ordinarily, optimum production is obtained after incubation periods of about 3-11 days. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium.

When fermentation is complete, the rachelmycin is extracted from the whole broth with a water-immiscible organic solvent, the organic extract is concentrated, and the rachelmycin is precipitated by dilution of the concentrated extract with a suitable antisolvent. Although polar solvents such as n-butanol may be used for the extraction, intermediate polarity solvents such as ethyl acetate, amyl acetate or methyl isobutyl ketone are more selective and, therefore, preferred. The rachelmycin extracts best under slightly alkaline conditions (pH 9.5-10), with poor extraction being noted under acidic conditions. Filter aid is preferably added to the extraction mixture and the mixture then filtered. The organic phase is concentrated and diluted with an appropriate antisolvent to precipitate out the rachelmycin. Suitable antisolvents can be determined by simple test and include such organic non-solvents for rachelmycin as diethyl ether, benzene and liquid aliphatic hydrocarbons such as n-hexane, n-heptane or Skellysolve B (tradename of Skelly Oil Co for isomeric hexanes).

Further purification of the rachelmycin antibiotic may be carried out using conventional techniques such as chromatography over Sephadex LH-20 (tradename of Pharmacia Fine Chemicals Inc. for a modified dextran adsorbent).

BIOLOGICAL PROPERTIES

Rachelmycin inhibits the growth of various Gram-positive bacteria, e.g. *Staphylococcus aureus*, and can thus be used alone or in combination with other antibacterial agents to prevent the growth of, or reduce the number of, sensitive pathogenic bacteria. In addition to usefulness as an antibacterial agent for treatment of infectious diseases in animals (including man), the rachelmycin antibiotic may be employed in wash solutions for sanitation purposes, e.g. for washing hands and disinfecting various laboratory, dental and medical equipment, and as a bacteriostatic rinse for laundered clothes.

Rachelmycin has also been found to induce bacteriophage production in lysogenic strains of bacteria, thus indicating antitumor activity. Additionally, in tests against various transplantable rodent tumor systems, rachelmycin exhibited significant tumor inhibitory effects against P-388 leukemia, L-1210 leukemia, Sarcoma 180, Walker 256 carcinosarcoma, B16 melanoma and Lewis lung carcinoma. Representative of such tests which demonstrate the ability of rachelmycin to inhibit the growth of animal tumors are the following:

TABLE 7

Treatment of L-1210 Leukemia with Rachelmycin in Mice*

| Dose** (mg/kg/inj.) | Regimen# | T/C % | Weight Difference T-C in g. | Survivors on Day 5 |
|---|---|---|---|---|
| 3.2 | 9 injections, days 1-9 | 114 | −3.0 | 6/6 |
| 1.6 | 9 injections, days 1-9 | 143 | −2.0 | 5/6 |
| 0.8 | 9 injections, days 1-9 | 136 | −2.6 | 6/6 |
| 0.4 | 9 injections, days 1-9 | 121 | −2.4 | 6/6 |
| 0.2 | 9 injections, days 1-9 | 121 | −1.7 | 6/6 |
| 0.1 | 9 injections, days 1-9 | 114 | −1.4 | 6/6 |
| 0.05 | 9 injections, days 1-9 | 114 | −0.8 | 6/6 |

*$BDF_1$ ♀ mice
**Cell dose = $10^6$ cells implanted ip
9 injections given ip; one each day for 9 consecutive days

TABLE 8

Treatment of P-388 Leukemia with Rachelmycin in Mice

| Dose (mg/kg/day) | MST (days) | Effect MST (% T/C) | Average Weight Change, T-C in g. | Survivors on Day 5 |
|---|---|---|---|---|
| 0.32 | 9.0 | 90 | −1.2 | 6/6 |
| 0.16 | 12.5 | 125 | −0.4 | 5/6 |
| 0.08 | 16.0 | 160 | +0.6 | 6/6 |
| 0.04 | 17.0 | 170 | +0.1 | 6/6 |
| 0.02 | 15.5 | 155 | +1.1 | 6/6 |
| 0.01 | 14.0 | 140 | +1.3 | 6/6 |
| Control | 10.0 | — | +3.3 | 10/10 |

Host: $CDF_1$ ♂ mice
Treatment: 9 injections given ip; one each day for 9 consecutive days
Tumor inoculum: $10^6$ ascites cells implanted ip
Evaluation: MST = median survival time
Effect: % T/C = MST treated ÷ MST control × 100
Criteria: T/C ≥ 125 considered significant antitumor effect Table 7 indicates that rachelmycin exhibits activity against L-1210 leukemia in mice at doses of 1.6 and 0.8 mg/kg/day. Table 8 shows activity of rachelmycin against P-388 leukemia in mice at doses of 1.6 to 0.01 mg/kg/day. The dose levels in Tables 7 and 8 indicate that rachelmycin is a remarkably potent antitumor agent.

According to another aspect of this invention, a method is provided for therapeutically treating an animal host affected by a Gram-positive bacterial infection or by a malignant tumor sensitive to rachelmycin which comprises administering to said host an effective antibacterial or tumor-inhibiting dose of rachelmycin.

According to still another aspect of this invention, a pharmaceutical composition is provided which comprises an effective antibacterial or tumor-inhibiting amount of rachelmycin in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the rachelmycin antibiotic used will vary according to the particular composition formulated, the mode of application and the particular situs, host and disease being treated. In general rachelmycin is injected intraperitoneally, intravenously, subcutaneously or locally. Many factors that modify the action of the drug will be taken into account by those skilled in the art, e.g. age, body weight, sex, diet, time of administration, route of administration, rate of excretion, condition of the patient, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the invention.

EXAMPLE 1

Fermentation of Rachelmycin with Strain C-329

A. Shake-flask Fermentation

Streptomyces sp. strain C-329 variant 70 is grown in a test tube on a sterile agar slant medium consisting of 2.0 g. glucose, 20.0 g. oatmeal, 2.0 g. soy peptone and 20.0 g. agar, made up to 1.0 liter with distilled water. After seven days of incubation at 27° C., growth from the surface of the slant is transferred to a 500 ml. Erlenmeyer flask with 100 ml. of sterile medium consisting of 50.0 g. corn starch, 10.0 g. Pharmamedia (cottonseed meal; Traders Oil Mill Co., Fort Worth, Tex.), 10.0 g. Mellasoy (soy flour; Swift Chemical Co., Oak Brook, Ill.) and 30 g. $CaCO_3$ made up to 1.0 l with distilled water. This vegetative culture is incubated at 27° C. for 48 hours on a Gyrotory Tier shaker (Model G53, New Brunswick Scientific Co., Inc.) set at 210 rev./min. describing a circle with a 5.1 cm. diameter. Four milliliters of vegetative culture is transferred to a 500 ml. Erlenmeyer flask containing 100 ml. of sterile production medium consisting of 50 g. glucose, 20.0 g. Pharmamedia, 10.0 g. Fermo 30 autolyzed yeast (Yeast Products Inc.) and 10.0 g. $CaCO_3$, made up to one liter with distilled water. This production culture is incubated at 30° C. on the previously described shaker for 8 days at which time rachelmycin is at a maximum level found both in mycelium and extracellular fluid.

B. Stir-jar Fermentation

A vegetative culture, prepared as in Part A above is incubated for 72 hours, and 80 ml. is transferred to a 2 l Erlenmeyer flask with 800 ml. of the same sterile medium. This culture is incubated at 27° C. on a shaker for 48 hours. At this time, 750 ml. is transferred to 10 l of sterile production medium in a 14 l capacity stir-jar fermentor. The production medium consists of 50.0 g. glucose, 20.0 g. Pharmamedia, 5.0 g. Fermo autolyzed yeast, 5.0 g. Maggi yeast extract (Nestle Co., White Plains, N.Y. ), 0.1 ml. Hodag F1 silicone antifoam (Hodag Chemical Corp., Skokie, Ill.) and 10.0 g. $CaCO_3$ per liter of distilled water. The stir-jar fermentor is installed in a Fermentor Drive Assembly (Model FS-614, New Brunswick Scientific Co., Inc., New Brunswick, N.J.). The temperature is maintained at 32° C., the air flow rate is 8 liters/min. and the agitator is set at 360 rev./min. Hodag F1 antifoam is fed automatically as required to control foaming. At 163 hours the incubation is terminated for extraction of rachelmycin.

C. Tank Fermentation

To prepare rachelmycin in a tank fermentation, 3.78 l of vegetative culture of strain C-329 variant 70 is transferred to a tank fermentor containing 37.8 l of sterile medium consisting of 50.0 g. glucose, 20.0 g. Pharmamedia, 10.0 g. Fermo 30 autolyzed yeast and 10.0 g $CaCO_3$ per liter of tap water. The temperature is maintained at 32.2° C., the air flow rate is 65.1 liters/min., the back-pressure is 1 atm. and the agitation rate is 300 rev./min. After 250 hours the fermentation is terminated for extraction of rachelmycin.

For a larger tank fermentation, 151 l of vegetative culture is transferred to a fermentor containing 3030 l of medium consisting of 50.0 g. glucose, 20.0 g. Pharmamedia, 10.0 g. $CaCO_3$ and 5.0 ml. Antifoam A emulsion (Dow Corning Corp., Midland, Mich.) per liter of tap water. The temperature is maintained at 32.2° C., the air flow rate is 1420 liters/min., the back pressure is 1 atm. and the agitation rate is 155 rpm. The fermentation is terminated at 180 hours for isolation of rachelmycin.

EXAMPLE 2

Fermentation of Rachelmycin with Strain C-22,437

A. Shake-Flask Fermentation

Strain C-22,437 is maintained and transferred in test tubes on agar slants of yeast extract-malt extract medium consisting of 4 g. glucose, 4 g. yeast extract, 10 g. malt extract and 20 g. agar, made up to one liter with distilled water. With each transfer, the agar slant culture is incubated for seven days at 27° C. To prepare an inoculum for fermentation studies, the surface growth from a slant culture is transferred to a 500 ml. Erlenmeyer flask containing 100 ml. of sterile medium consisting of 30 g. glucose, 30 g. Mellasoy (soy flour; Swift Chemical Co., Oak Brooke, Ill.) and 3 g. $CaCO_3$ made up to one liter with distilled water. This vegetative culture is incubated at 27° C. for 48 hours on a Gyrotory tier shaker (Model G-53, New Brunswick Scientific Co., Inc.) set at 230 rev./min. describing a circle with a 5.1 cm. diameter. Four milliliters of vegetative culture is transferred to a 500 ml. Erlenmeyer flask containing 100 ml. of sterile production medium consisting of 30 g. glucose, 40 g. Mellasoy and 3 g. $CaCO_3$ made up to one liter with distilled water. The production culture is incubated at 27° C. on a shaker such as used for the vegetative culture set at 210 rev./min. for ten days at which time rachelmycin is accumulated in the mycelium and the extracellular fluid.

B. Stir-jar Fermentation

A vegetative culture is prepared with strain C-22,437 as described previously and 32 ml. is transferred to a two liter Erlenmeyer flask with 400 ml. of the same sterile medium. This culture is incubated at 27° C. on a shaker for 48 hours. At this time, 500 ml. is transferred to a 14 liter capacity fermentor with 10 liters of sterile production medium consisting of 20 g. glucose, 30 g. Mellasoy, 0.1 ml. Hodag F1 silicone antifoam and 3 g. $CaCO_3$ per liter of distilled water. The stir-jar fermentor is installed in a Fermentor Drive Assembly as previously described. The temperature is maintained at 27° C., the air flow rate is 6 liters/min. and the agitator is set at 360 rev./min. Rachelmycin is found in the mycelium and extracellular fluid after 260 hours of incubation.

C. Tank Fermentation

To prepare rachelmycin in a tank fermentor, 1.89 liters of vegetative culture is transferred to a tank containing 37.8 liters of medium consisting of 50 g. glucose, 50 g. Mellasoy, 3 g. $CaCO_3$ and 0.1 ml. Hodag F1 antifoam per liter of tap water. The temperature is maintained at 27.2° C., the air flow rate is 82 liters/min., the back-pressure is 1 atm. and the agitation rate is 375 rev./min. Fermentation is terminated at 140 hours for isolation of rachelmycin.

For a larger tank fermentation, 151 liters of vegetative culture is transferred to a tank containing 3030 liters of medium consisting of 50 g. glucose, 40 g. Mellasoy, 3 g. $CaCO_3$ and 0.1 ml. Hodag F1 antifoam per liter of tap water. The temperature is maintained at 27.2° C., the air flow rate is 1980 liters/min., the back pressure is 1 atm., and the agitation rate is 155 rev./min. The tank is terminated at 140 hours for isolation of rachelmycin.

EXAMPLE 3

Extraction of Rachelmycin from Strain C-329

Whole broth from fermentation of strain C-329 variant 70 was stirred with an equal volume of methyl isobutyl ketone at broth pH (generally 8–8.5) for one hour. A large amount of diatomaceous earth filter aid was thoroughly stirred into the mixture, and the latter was then filtered on a filter aid mat with vacuum. The organic phase in the filtrate was separated, concentrated to a small volume under vacuum, and diluted with diethyl ether. The crude rachelmycin precipitate which formed was collected and air-dried.

EXAMPLE 4

Extraction of Rachelmycin from Strain C-22,437

The whole broth (8 l) from fermentation of strain C-22,437 was adjusted from pH 7.6 to 9.7 with dilute aqueous NaOH and extracted with an equal volume of ethyl acetate. (In other runs methyl isobutyl ketone was found to perform equally well and to have the additional property of lower volatility and consequently less loss during filtration of the mat). The mixture was heavily admixed with inert diatomaceous earth filter aid and filtered under vacuum on a mat formed of the same material. The phases in the filtrate were separated, and the aqueous phase was discarded. The organic phase was evaporated to a small volume and diluted with Skellysolve B. The precipitate which formed was collected by filtration and dried in vacuo to give 6.38 g.

crude yellow solids, effective vs. the L-1210 mouse leukemia system at doses down to 0.4 mg/kg/day.

EXAMPLE 5

Large Scale Extraction of Rachelmycin from Strain C-22,437

A large scale whole fermentation broth (2971 l) was divided into two 1485 l aliquots. The first was adjusted to pH 9.5 with 30% NaOH and extracted as in Example 4 with ethyl acetate. The extraction mixture was filtered on a UF-1 rotary vacuum filter using diatomaceous earth filter aid both admixed and as mat. During the process virtually all of the ethyl acetate evaporated and the filtrate required re-extraction with 700 l additional solvent. The phases were separated by centrifugation, and the ethyl acetate layer was concentrated to 1.04 l and diluted with Skellysolve B to give 18 g. crude rachelmycin active vs. the L-1210 system down to 0.5 mg/kg/day dosage. (During workup of the ethyl acetate fraction, various amounts of yellow pigmented solids, largely inactive, precipitated and had to be removed). The second aliquot was extracted and worked up in the same way with a mixture of 600 l ethyl acetate and 750 l methyl isobutyl ketone. In this case the filtrate was obtained as an emulsion which was resolved as above. The organic phase was concentrated to 2.43 l and diluted with excess Skellysolve B to give 60 g. of precipitated solid rachelmycin active vs. the L-1210 system down to 1.6–3.2 mg/kg/day dosage. An additional 520 g. inactive material precipitated and was removed during processing.

EXAMPLE 6

Purification of Rachelmycin

Sephadex LH-20 (350 g) was stirred gently with 100% methanol and left to stand for 24 hours to ensure full equilibration. This mixture was then used to slurry pack a Fisher-Porter column having 5 cm diameter×40 cm height bed dimensions and the column was then washed using downward flow to settle and equilibrate the bed. By use of a column extender at the top, the bed could be brought to the top of the column and capped. A composite of crude active rachelmycin solids (34.2 g) was sonicated with 200 ml 1:1 methylene chloride:methanol (v/v) to give 7.3 g of insoluble and inactive material upon filtration. The liquor was evaporated and the residue combined with an additional 3 g composited active crude rachelmycin solids. This was taken up in a mixture of 100 ml. methanol and 20 ml. methylene chloride, sonicated, and filtered to afford another 3.2 g inactive solids. Half of the filtrate was applied to the column and the latter was developed by downward flow with 100% methanol at 1 ml/min. for the first 24 hours and a 2 ml/min. thereafter. Fractions of 10 ml. were collected in test tubes on a fraction collector. These were analyzed by full scan of the liquors in a UV spectrophotometer in the range of 210–600 nm. A variety of pigments eluted first, but the activity appeared in tubes 220–330 and was characterized by a distinctive UV absorption maximum at 379 nm. Crystalline material (11 mg) deposited from these tubes on standing and was found by PMR analysis to be substantially pure rachelmycin.

This invention is capable of industrial application.

We claim:

1. A process for producing rachelmycin which comprises cultivating a rachelmycin-producing strain of Streptomyces sp. having the identifying characteristics of ATCC 31128 or *Streptomyces anandii* subsp. *arraffinosus* having the identifying characteristics of ATCC 31431, or a mutant thereof, in an aqueous nutrient medium under submerged aerobic conditions until a substantial amount of rachelmycin is produced by said organism in said culture medium.

2. The process according to claim 1 wherein the rachelmycin-producing strain is Streptomyces sp. ATCC 31128 or a mutant thereof.

3. The process according to claim 1 wherein the rachelmycin-producing strain is *Streptomyces anandii* subsp. *arraffinosus* ATCC 31431 or a mutant thereof.

4. The process according to claim 1, 2, or 3 which includes the additional step of isolating the rachelmycin from the culture medium.

* * * * *